(12) United States Patent
Shearer et al.

(10) Patent No.: US 12,152,577 B2
(45) Date of Patent: Nov. 26, 2024

(54) INJECTION-MOLDED HOSE

(71) Applicant: Integra Biosciences AG, Zizers (CH)

(72) Inventors: Daniel Shearer, Pratval (CH); Noel Pasquier, Landquart (CH); Andreas Staedler, Felsberg (CH)

(73) Assignee: Integra Biosciences AG, Zizers (CH)

( * ) Notice: Subject to any disclaimer, the term of this patent is extended or adjusted under 35 U.S.C. 154(b) by 0 days.

(21) Appl. No.: 17/467,796

(22) Filed: Sep. 7, 2021

(65) Prior Publication Data
US 2022/0074404 A1   Mar. 10, 2022

(30) Foreign Application Priority Data

Sep. 8, 2020   (CH) ..................................... 1113/20

(51) Int. Cl.
| | |
|---|---|
| *F04B 43/08* | (2006.01) |
| *B29C 45/00* | (2006.01) |
| *B29C 45/03* | (2006.01) |
| *B29K 83/00* | (2006.01) |
| *B29L 23/00* | (2006.01) |

(52) U.S. Cl.
CPC .......... *F04B 43/08* (2013.01); *B29C 45/0001* (2013.01); *B29C 45/0053* (2013.01); *B29C 45/03* (2013.01); *B29C 2045/0087* (2013.01); *B29C 2045/0089* (2013.01);
(Continued)

(58) Field of Classification Search
CPC ......... F04B 43/08; B29C 45/00; B29C 45/03; B29L 2030/00; B29L 2023/005; B29L 2023/007
See application file for complete search history.

(56) References Cited

U.S. PATENT DOCUMENTS 5,098,261 A  *  3/1992  Bertoncini ............ F04B 43/082
                                                      417/474
6,406,267 B1 *  6/2002  Mondiere ........... F04B 43/0072
                                                      417/53
(Continued)

FOREIGN PATENT DOCUMENTS

| EP | 2 754 462 | 7/2014 |
|---|---|---|
| EP | 3 103 614 | 12/2016 |
| WO | 00/57941 | 10/2000 |

OTHER PUBLICATIONS

European Search Report dated Mar. 9, 2021 in priority Switzerland patent application 01113/20.

*Primary Examiner* — Connor J Tremarche
(74) *Attorney, Agent, or Firm* — Andrus Intellectual Property Law, LLP (57) ABSTRACT

Disclosed and described is a hose for attachment to a dispensing cartridge for placement in a peristaltic pump, for stretching over a rotor of the peristaltic pump, and for conveying a medium by external mechanical deformation of the hose. The hose has a length of preferably 20 mm to 200 mm, an internal cross-sectional area of 0.07 to 7.07 mm², and a wall thickness of 0.3 mm to 2.2 mm. Thickenings are formed at both ends of the hose and the distance between the thickenings is 40 mm to 100 mm. According to the invention, it is provided that the hose is manufactured by an injection molding process, the inner cross-sectional area has a tolerance of at most±33%, and the hose is suitable for closing completely when stretched over the rotor with a tension force of 1 to 10 N.

9 Claims, 4 Drawing Sheets

(52) U.S. Cl.
CPC ............... *B29C 2045/0093* (2013.01); *B29C 2793/0027* (2013.01); *B29K 2083/005* (2013.01); *B29L 2023/007* (2013.01)

(56) References Cited

U.S. PATENT DOCUMENTS

| | | |
|---|---|---|
| 9,909,579 B2 * | 3/2018 | Gledhill, III ........ F04B 43/1284 |
| 10,330,224 B2 | 6/2019 | Werner |
| 2010/0300300 A1 * | 12/2010 | Denisart ............... F16K 11/027 |
| | | 99/302 R |
| 2011/0014075 A1 * | 1/2011 | Reif .................... F04B 43/1261 |
| | | 417/477.12 |
| 2012/0034117 A1 | 2/2012 | Pfouts et al. |
| 2013/0327428 A1 * | 12/2013 | Siddhamalli ............ F16L 11/06 |
| | | 428/36.9 |
| 2017/0298921 A1 * | 10/2017 | Loth ................... F04B 43/1253 |
| 2018/0171996 A1 * | 6/2018 | Cheung ............... F04B 43/1223 |
| 2020/0346216 A1 * | 11/2020 | Marchand ............... F16L 11/04 |

* cited by examiner

Fig. 7

INJECTION-MOLDED HOSE

CROSS REFERENCE TO RELATED APPLICATION

The present application claims priority to Switzerland Patent Application 01113/20 filed Sep. 8, 2020.

TECHNICAL FIELD OF THE INVENTION

The invention relates to a hose, in particular for mounting in a dispensing cartridge, in accordance with the preamble of claim 1. Furthermore, the invention relates to a hose connection comprising such a hose, a method of manufacturing such a hose, and a use of such a hose.

BACKGROUND OF THE INVENTION

Dispensing cartridges disclosed in the prior art for use in a peristaltic pump have a multi-part construction. The dispensing cartridge comprises two to three individual cartridges as well as hoses, each of which leads from the first cartridge via the second cartridge to a possible third cartridge (see FIG. 3). The number of hoses in a dispensing cartridge, arranged side by side in a row and parallel to one other, is generally at most 16. The hoses between the first and second or between the second and third cartridges lie on the rotor of a peristaltic pump. Due to the fact that the hoses arranged on the rotor are subject to greater stresses, these hoses can be provided separately and do not need to cover the entire length from the first to the last cartridge. In addition to the hoses, the first cartridge also contains dispensing tips which convey the medium transported in the hoses to the outside. Connectors are provided in the third cartridge to interface with the container in which the medium to be dispensed is stored. In a dispensing cartridge disclosed in the prior art, each cartridge must be individually attached to the peristaltic pump. In the case of a three-part construction of the dispensing cartridge, this leads to three successive work steps which must be carried out, both when attaching to and detaching from the peristaltic pump.

The hoses used in a dispensing cartridge must have a flexible wall. The medium within the hoses is transported by means of peristalsis. This means that due to the deformation of the hose, the medium inside the hose is conveyed specifically in one direction. The hoses in the dispensing cartridge must be stretched on the rotor of the peristaltic pump with a certain tension in order to allow the hoses to be deformed by the rotor at all, thereby allowing a medium to be dispensed.

Hoses for use in dispensing cartridges are manufactured by extrusion. This method has the disadvantage that the tolerance in the diameter of the hose and thus the differences between the inner diameters between hoses are relatively large. This in turn leads to flow rates that differ between hoses under the same conditions. Equalization of the flow rate between the hoses is achieved by changing the hose length. The change in length causes a change in the cross-section and at the same time in the volume, whereby the cross-section in turn has a direct influence on the flow rate of the individual hose. The length, and therefore the diameter, of each hose can be adjusted by varying the tension applied to the hose in order to achieve identical flow rates between hoses. For this reason, tension elements are provided for each individual hose on cartridges currently in use. An adjusting screw on these tension elements allows the tension force applied to the hose to be adjusted and, at the same time, the length and diameter of the hose.

One of the reasons for the need to adjust the tension force for each hose individually is the different diameter of the hoses, as mentioned above. The currently common process for manufacturing hoses for use in dispensing cartridges is extrusion. This method has the disadvantage that when a hose is manufactured, the diameter of the hose depends on the manufacturing speed. This means that even slight changes in the speed of the extrusion product result in a different hose diameter.

Both the adjustment of the tension force for each individual hose and the step-by-step attachment of the cartridges result in a considerable amount of work when installing the dispensing cartridge on a peristaltic pump. This time is included directly in production time, in turn resulting in an inefficient production process.

The flow rate through a hose depends on its diameter and thus, among other things, on the tension force applied to it. Since the diameter of the hoses varies due to the manufacturing method, the tension force must accordingly be set individually for each hose. This is the only way to ensure that the large number of hoses used have the same delivery rate.

WO 00/57941 discloses a hose for use in an infusion pump which is manufactured in an injection molding process, preferably from silicone. The hose has a first section which is placed on the rotor of the infusion pump. As the rotor turns, the hose is pressed onto the opposite hose bed of the infusion pump, thus clamping the hose off. A second portion of the hose has an inner surface texture which differs from that of the first portion. This different inner surface structure in the second section allows optical measurements to be made while using the hose in an infusion pump.

The outer surface of the hoses may have shoulders formed thereon, which serve to position the hoses in an infusion pump. The outer diameter of the hose is about 0.4 cm, resulting in an outer cross-sectional area of about 12.5 mm². The hose is attached and held to the infusion pump at its two ends using a clamping device.

Object

It is therefore one task of the present invention to provide a hose which has the desired flow rate without the need to make any adjustment to the hose. At the same time, a hose should be provided which can be used in a peristaltic pump without a hose bed and which has a long service life.

A hose connection should also be provided which also ensures a desired flow rate without having to make an adjustment on any hose section of the hose connection. A further task of the present invention is to disclose a method of manufacturing and a use of such a hose.

DESCRIPTION

The above-mentioned tasks are solved in accordance with the invention, in part, using a hose characterized in that it is produced by an injection molding process and a suitable tolerance in its internal cross-sectional area.

The invention relates to a hose for attachment to a dispensing cartridge for placement in a peristaltic pump and for stretching over a rotor of the peristaltic pump and conveying a medium by external mechanical deformation of the hose. The hose has a length preferably from 20 mm to 200 mm, an internal cross-sectional area from 0.07 to 7.07 mm², and a wall thickness from 0.3 mm to 2.2, mm, preferably from 0.3 to 1.5 mm. Thickenings are formed at the ends of the hose and the distance between the thickenings is between 40 and 100 mm. According to the invention, the hose is manufactured using an injection molding process and is suitable for closing completely when stretched over the rotor with a tension force of 1 to 10 N. The internal cross-sectional area of the hose has a maximum tolerance of ±33%.

The injection molding process produces a single-piece hose. This means that the thickenings are materially bonded to the hose by means of the manufacturing process. This makes it possible to produce a hose with thickenings at its ends in a single process step. No subsequent post-processing is necessary. According to the present invention, the manufacturing process of injection molding has the advantage that the tolerances of the dimensions of a hose manufactured in this way are very small in comparison with other manufacturing processes. In the case of hoses for attachment to a dispensing cartridge for placement in a peristaltic pump, the small tolerance has a significant influence on the use of the hoses. This is due to the fact that a hose in a peristaltic pump is intended to dispense a certain amount of fluid. This quantity should be as constant as possible, not only over time but also between hoses. The internal cross-sectional area of a hose has a direct influence on the amount of liquid that is pumped through the hose in a peristaltic pump. Changing the internal cross-sectional area of hoses in relation to one other results in correspondingly different flow rates through these hoses. In the state of the art, the difference in the internal cross-sectional areas of hoses must be compensated for by adjusting the tension force on the hoses. This requires the tension force to be adjusted individually for each hose. With a small tolerance for the inner cross-sectional area, individual adjustment of the tension force on the hose can be eliminated, which greatly facilitates the use of a dispensing cartridge with such hoses. By using injection molded hoses, a time-consuming step in the manufacturing of a dispensing cartridge can be eliminated altogether. At the same time, the ratio between the internal cross-sectional area of 0.07 to 7.07 mm$^2$ and the wall thickness of 0.3 to 2.2 mm allows the hose to be completely closed by stretching the hose over the rotor. Due to this feature, a hose bed can be dispensed with in the peristaltic pump. The hose is thus able to close on the basis of the pretensioning force alone.

The figure of 33% is the result of a deviation in the inner diameter of 0.05 mm with an inner cross-sectional area of 0.07 mm$^2$. Thus, a deviation in the inner diameter of 0.05 mm for a hose with a diameter of 0.3 mm leads to a change in the inner cross-sectional area of 33%. The larger the inner diameter, the smaller the change in the inner cross-sectional area, with a constant tolerance in the inner diameter of 0.05 mm. With a cross-sectional area of 7.07 mm$^2$ and an inner diameter of 3 mm, a deviation in the inner diameter by 0.05 mm causes a change in the inner cross-sectional area of 3.3%.

The tolerance should be understood in such a way that, given a normal distribution of the internal cross-sectional areas of hoses in accordance with the invention, 95% of the hoses have an internal cross-sectional area which lies within the defined tolerance range. Statistically, the tolerance defined and used here is twice the standard deviation. In order to be able to make a statement about the tolerance of the internal cross-sectional areas of a hose, a statistical evaluation must be carried out, for which an appropriate minimum number of hoses must be made available.

In a preferred embodiment, the internal cross-sectional area of the hose has a tolerance of no more than ±13.3%, particularly no more than ±6.7%. A tolerance of 13.3% for the inner cross-sectional area corresponds to a change of 0.02 mm for an inner diameter of 0.3 mm. At an inner diameter of 3 mm, the change in the inner diameter by 0.02 mm causes a change in the inner cross-sectional area by 1.3%. A tolerance of 6.7% for the inner cross-sectional area corresponds to a change of 0.01 mm in the inner diameter of 0.3 mm. A change by 0.01 mm in an inner diameter of 3 mm leads to a change in the inner cross-sectional area of 0.7%.

In a further preferred embodiment, the hoses have an internal cross-sectional area of 0.502 to 1.767 mm$^2$ and the internal cross-sectional area has a tolerance of ±12.5%. An inner cross-sectional area of 0.502 to 1.767 mm$^2$ corresponds to an inner diameter of 0.8 to 1.5 mm. A change in the inner diameter of 0.05 mm leads to a change in the inner cross-sectional area of 12.5% for an inner diameter of 0.8 mm.

Advantageously, the material of the hose has a Shore hardness ranging from 20 to 80 Shore-A, preferably from 35 to 65 Shore-A, and more preferably from 45 to 55 Shore-A. The Shore hardness is a standardized material parameter defined for elastomers and plastics. For soft elastomers, the value is given in Shore-A, with the scale ranging from 0 for soft to 100 for hard. For use in a peristaltic pump, the selection of a suitable hardness for the hose material is of great importance.

The material of the hose preferably has a density ranging from 0.8 to 2.5 g/cm$^3$, in particular from 1.05 to 1.75 g/cm$^3$. Based on the dimensions given above and the density proposed here, a mass is obtained for the hose which allows easy handling. Also, an arrangement of multiple hoses in a dispensing cartridge would still have such a small mass that the ability to operate the dispensing cartridge with only one hand would still be possible.

The material of the hose preferably comprises a plastic from the group of polyvinyl chlorides (PVC). PVC has material properties that meet the requirements of the hose. As a thermoplastic, PVC is ideal for injection molding, among other things.

In a further preferred embodiment, the material of the hose comprises silicone. Silicone also meets all the requirements for the material of the hose. In addition, silicone offers better environmental sustainability than plastics.

As mentioned above, the hoses are intended to be placed in a dispensing cartridge. Advantageously, the thickenings on the hose are each designed to form a positive connection with the dispensing cartridge. This allows the hoses to be replaced with minimal effort. At the same time, the positive connection allows the hoses to always be installed in the same place, so that no further control of the hose length or the like remains necessary. The thickenings can have different shapes. Conceivably, the shape of the thickenings may be cuboidal, cubic, spherical, or cylindrical, this being a non-exhaustive list of shapes. In the case of a cuboid or cylindrical thickening, the longitudinal axis of the cuboid or cylindrical axis of the cylinder always runs parallel with the longitudinal direction of the hose.

In a further preferred embodiment, the hoses has a wall thickness of 0.3 mm to 1.2 mm. The wall thickness has a direct influence on the material costs. The thinner the wall, the smaller the amount of material required in the injection molding process. In addition to the amount of material required, the wall thickness also has an influence on the necessary squeezing force of the hose, i.e. the force that must be applied to ensure that the hose is tight due to its deformation. If the wall thickness is greatly increased, the required flexibility of the hose can no longer be guaranteed after a certain point. This in turn plays a significant role in the use of the hose in a peristaltic pump.

Preferably, the hose has a length from 20 mm to 70 mm. The length of the hose affects the total resistance to the fluid as it flows through the hose. To reduce the resistance to the liquid, the length of the hose can be reduced. With a shorter hose, the same amount of liquid can be pumped with a smaller amount of work.

In another embodiment, said hoses may be arranged side by side and connected to one other. The hoses can be arranged parallel to one other. The interconnected hoses are preferably all in the same plane. The production is carried out using an injection molding process in this case as well. This enables the production of all hoses, including the connection between these hoses, in a single process step. Advantageously, the hoses connected to one other in this way are all of the same length.

A second aspect of the invention relates to a hose connection comprising a first hose in accordance with the invention and a second hose. The second hose serves as an extension of the first hose. Advantageously, the first hose and the second hose are made of the same material. The first hose is further provided for mounting in a dispensing cartridge. The second hose, on the other hand, forms all or part of the connection between the dispensing cartridge and a container in which the liquid to be dispensed is stored.

In a preferred embodiment, the first hose forms a materially interlocking connection with the second hose. This creates a firm connection between the hoses, which can withstand higher loads. Due to the material-locking connection, there the two hoses are clearly assigned to one another.

In a further preferred embodiment, the second hose is overmolded onto the first hose. This means that both the first and the second hose are manufactured in an injection molding process. This allows the same materials to be used, resulting in material properties that are consistent between the two hoses.

In another preferred embodiment, a connector is arranged between the first hose and the second hose, and the connector includes a positive connection to the first hose and the second hose. A connector may be provided for making the connection between the first hose and the second hose. This has the advantage that the two hoses can be produced without regard to the possibility of connecting them to another hose. The positive connection of the connector allows the hoses to be replaced at will.

Advantageously, the positive connection between the connecting piece and the two hoses is formed by a plug-in connection. A plug-in connection is an inexpensive connection option. The two hoses to be connected can have the same inner diameter, whereby the speed of the liquid transported in the hose remains approximately the same in both hoses.

A third aspect of the invention relates to a method of manufacturing a hose for attachment to a dispensing cartridge for placement in a peristaltic pump and for conveying a medium by external mechanical deformation of the hose, wherein the hose has a length of preferably 20 mm to 100 mm, an internal cross-sectional area of 0.07 to 7.07 mm$^2$, and a wall thickness of 0.3 mm to 2.2 mm. The hose is suitable to be closed completely when stretched over the rotor with a tension force of 1 N to 10 N. At the same time, the hose is intended to be manufactured in an injection molding process.

The manufacturing process of injection molding has the great advantage that the tolerances of the hose dimensions are much smaller than those of manufacturing processes currently used.

Another aspect of the invention relates to the use of a hose in accordance with the invention in a dispensing cartridge for placement in a peristaltic pump. The dosing of the liquid is effected by turning a rotor of the peristaltic pump. The hose is stretched over the rotor with a tension force sufficient to open and close the hose completely by the mere turning of the rotor, the hose is not pressed against a wall opposite the rotor, and thus the dosing of the liquid takes place.

Still another aspect relates to the use of a plurality of hoses in accordance with the invention in a dispensing cartridge for placement in a peristaltic pump, wherein the hoses are arranged parallel to each other and stretched over a rotor of the peristaltic pump.

The optional features mentioned can be implemented in any combination, provided they are not mutually exclusive. In particular, where preferred ranges are indicated, further preferred ranges result from combinations of the minima and maxima mentioned in the ranges.

BRIEF DESCRIPTION OF THE FIGURES

Example embodiments of the invention are described below by way of example with reference to the figures. The figures show schematic representations, not to scale, as follows.

DETAILED DESCRIPTION OF THE FIGURES

In the following, identical reference numbers stand for identical or functionally identical elements (in different figures). An additional apostrophe may be used to distinguish similar or functionally identical or functionally similar elements in a further embodiment.

Figure 1:
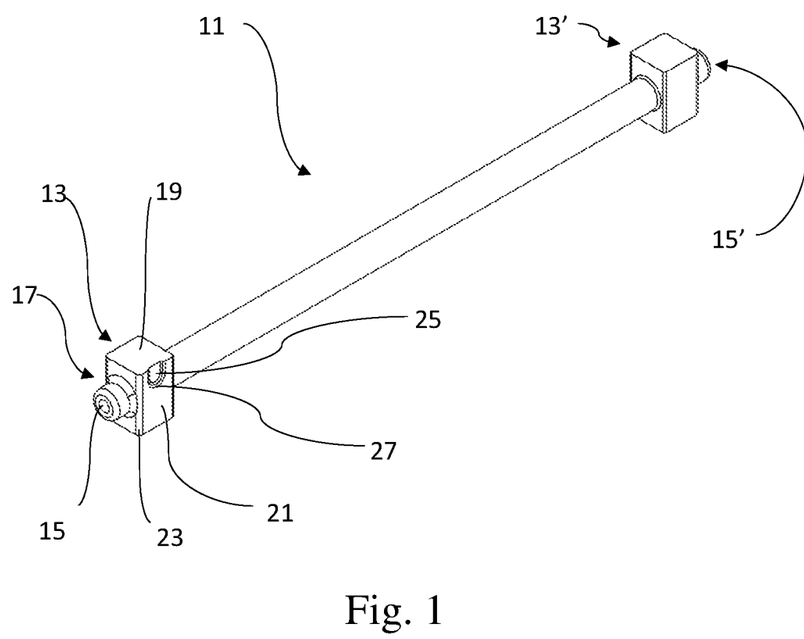
FIG. 1: a three-dimensional view of a hose with two thickenings.

FIG. 1 shows a hose 11 suitable for mounting in a dispensing cartridge. The task of the hose is to convey the medium it contains by means of its own mechanical deformation. The required flexibility of the hose is ideally ensured by using silicone as its material. The hose has a length between 20 and 200 mm and an outer diameter between 2.15 mm and 3.05 mm. The tolerance of the outer diameter is ±0.02 mm.

A cuboidal thickening 13 is provided at both ends of the hose, said thickening not extending to the respective end 15 of the hose, but rather extending to a point a short distance 17 away from the end of the hose. This distance is approximately equal to the width of the cuboid 13 which forms the thickening. The parallelepiped 13 has two opposing square sides 19 and four rectangular sides 21 of equal size, the rectangular sides 21 being larger than the square sides 19. The longitudinal edges 23 of the rectangular sides are perpendicular to the longitudinal direction of the hose and are also rounded.

The hose has a wall thickness from 0.5 mm to 0.9 mm. The inner diameter is between 1.15 and 1.25. The tolerance of the inner diameter is ±0.01 mm.

A recess 25 is provided on one rectangular side 21 of the parallelepiped 13. This extends from a short edge of the rectangular side to approximately the middle thereof, where it has a semicircular edge 27. The recess 25 has two steps in its depth.

Figure 2:
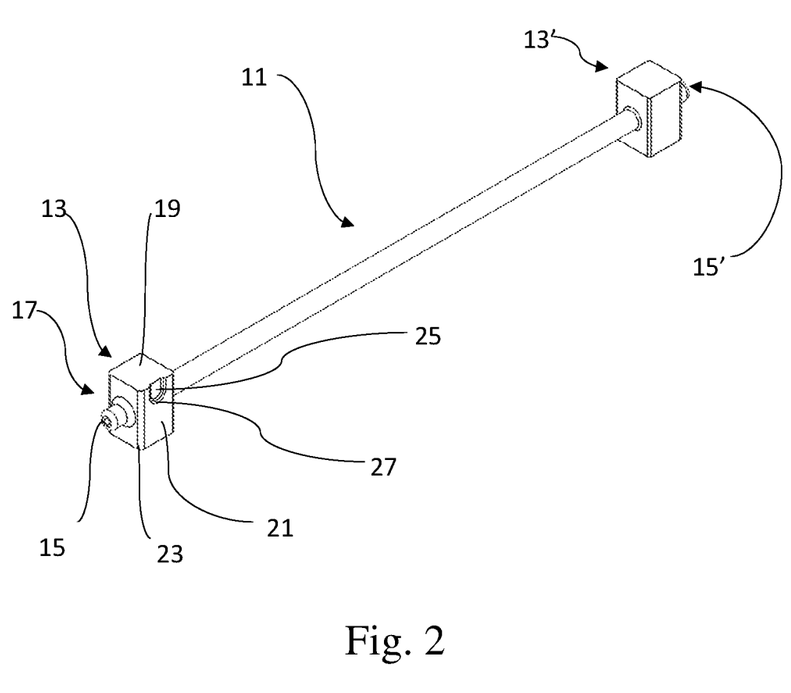
FIG. 2: a three-dimensional view of a hose with a smaller diameter than that shown in FIG. 1.

FIG. 2 shows a hose 11 which has a smaller diameter than that shown in FIG. 1. Both the inner diameter and the outer diameter of the 11 in FIG. 2 are smaller than those of the hose of FIG. 1. At the same length, the inner diameter of the hose in FIG. 2 is reduced to 0.85 mm to 0.95 mm. The tolerance of the inner diameter is also ±0.01 mm in this embodiment. The outer diameter is between 1.65 mm and 2.15 and has a tolerance of ±0.02 mm.

However, the thickenings 13 of the hose in FIG. 2 are approximately the same size as those of the hose in FIG. 1. There is therefore a different ratio between the cross-sections of the hose 11 and the thickening 13 for the two embodiments of the hose. Furthermore, the hoses 11 in FIGS. 1 and 2 have approximately the same length. This also results in a different length-to-diameter ratio between the two hoses.

Figure 3:
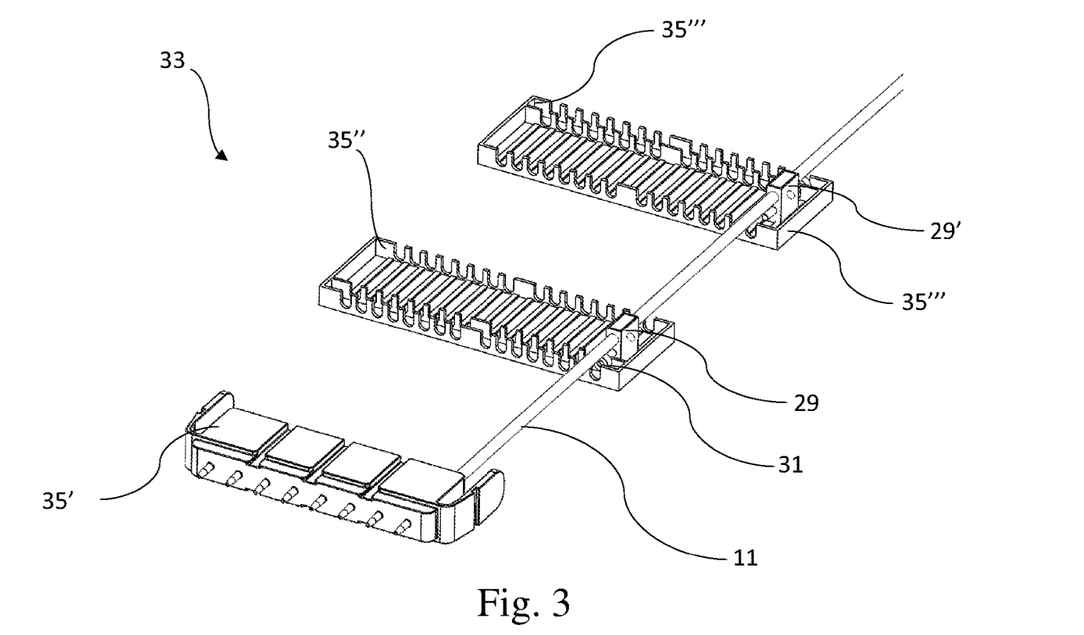
FIG. 3: a view of an arrangement for a dispensing cartridge with three cartridges in accordance with the present state of the art.

FIG. 3 shows a dispensing cartridge 33 comprising three cartridges 35. The cartridges 35 have a two-part construction with a housing and a cover, whereby in FIG. 3 only the housings of the cartridges 35 are shown. Recesses are provided in the second and third cartridges 35", 35" for receiving the hoses. In addition to these recesses at the inlet and outlet of the cartridge, both cartridges 35". 35" also have a tension element 29, 29' for each hose 11. In FIG. 3, only one hose 11 is shown, although in practice the number of hoses can be up to 16. The hoses 11 are all arranged side by side and parallel to one other. One end of the hose 11 is arranged in the first cartridge 35'. In the first cartridge 35', the hose transfers its contents to a dispensing tip which delivers the transported medium to the outside.

Figure 4:
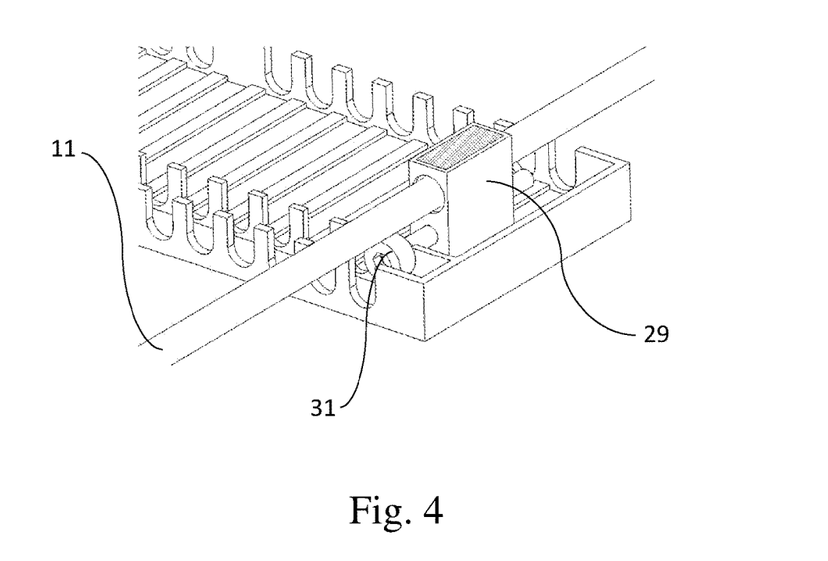
FIG. 4: a view of a tension element in a dispensing cartridge with hoses in accordance with the present state of the art.

In the prior art, hose 11 for use in a dispensing cartridge is manufactured using an extrusion process. These have a broader distribution of diameters than the hoses 11 in accordance with the invention. The result of this wide variation in the diameter of the hoses 11 is the need to adjust the tension force applied to the hose in the dispensing cartridge individually for each hose. For this purpose, tension elements 29, each with a set screw 31, are provided in currently available dispenser cartridges, which are shown in FIG. 4. The tension force and, at the same time, the length and diameter of each hose 11 can be adjusted by means of a set screw 31 provided for this purpose, so that all the hoses 11 have the same flow rate. Due to their manufacturing process, hoses 11 in accordance with the invention have such a narrow distribution of diameters that the same tension force can be applied to all hoses 11 in order to achieve a flow rate constant between hoses 11. This makes it possible to omit the tension elements 29 and set screws 31 in the dispensing cartridge when using hoses 11 in accordance with the invention.

Figures 5, 6:
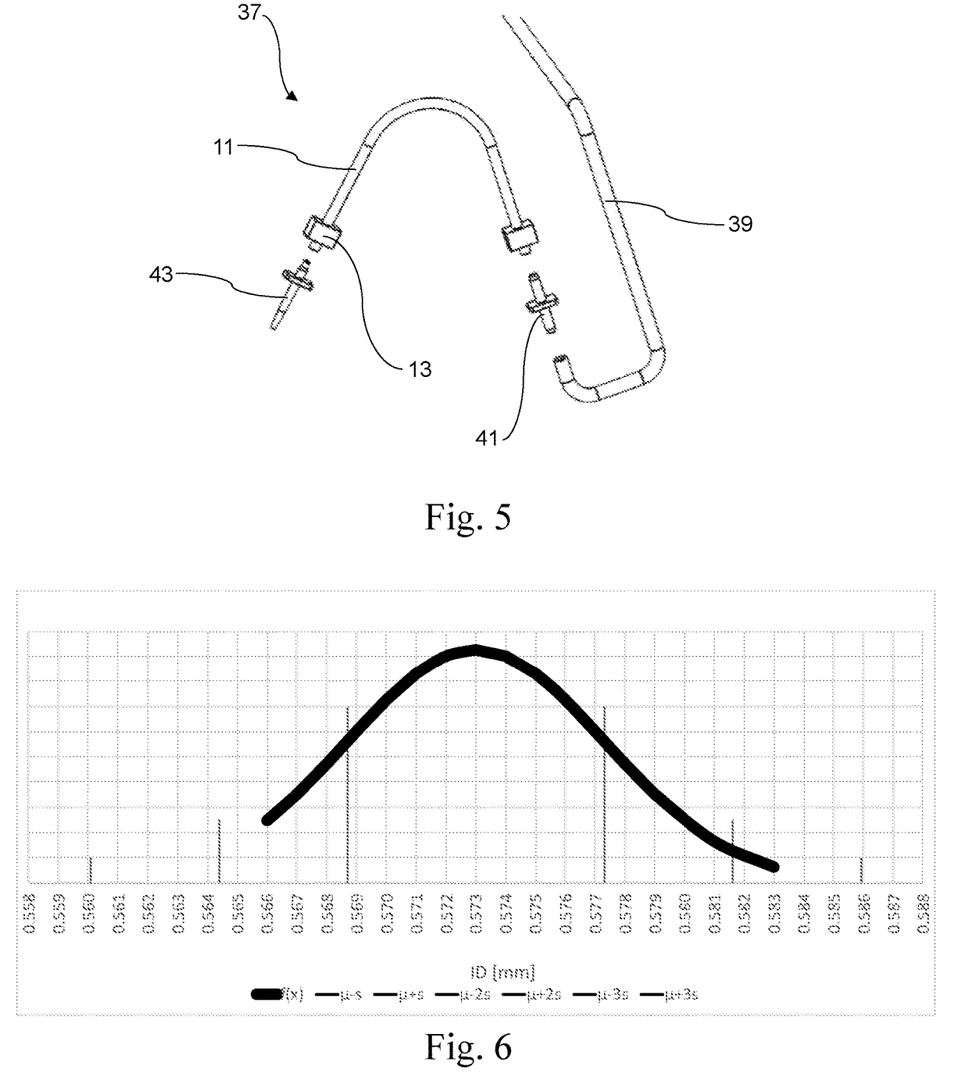
FIG. 5: an exploded view of a hose connection.
FIG. 6: a table showing the distribution of the internal diameters of hoses in accordance with the invention.

FIG. 5 shows a hose connection 37 comprising a first hose 11 in accordance with the invention and a second hose 39. A connector 41 is arranged between the first hose 11 and the second hose 39. This comprises a short hose section, the outer walls of which are conical at both ends. The connector 41 is intended to be inserted with both ends into one of the hoses 11, 37 to be connected. Drawing the hose over the connecting piece 41 establishes a frictional connection due to the conical shape of the outer wall of the connecting piece and the elasticity of the hose. A nozzle 43 may be attached to the other end of the first hose 11. Like the connector 41, this also has a conical outer wall so that it can also be inserted into the hose 11. At the end of the nozzle 43 opposite from the hose 11, there is provided a constriction of both the outer diameter and the inner diameter. This reduces the cross-sectional area, which inhibits dripping of the liquid during dispensing.

FIG. 6 shows a table showing the distribution of internal diameters of various hoses in accordance with the invention. As expected, the distribution of inner diameters shows a normal distribution with the mean inner diameter of 0.573 mm. The normal distribution allows a statement to be made about the definition of the tolerance. In a measurement series with a normal distribution, the tolerance represents the range of values in which 95% of the measured values are contained. In this case, 95% of the measured inside diameters are within a range of 0.573±0.0172 mm, which determines the tolerance of the diameter as ±0.0172 mm. The diameter of 0.573 mm chosen here is only one of many possible inner diameters of the hose in the range between 0.3 mm and 3.0 mm. Regardless of the choice of target diameter, the distribution of the diameters of a plurality of hoses results in a Gaussian normal distribution around the chosen target diameter.

To measure the internal cross-sectional area, the shape of the cross-sectional area must be determined. If the hose has a circular inner cross-section, the inner diameter can be used to infer the inner cross-sectional area. If the cross-section is rectangular or square, the side lengths must be measured to calculate the internal cross-sectional area. Since most hoses have a circular cross-section, the measuring method for determining the internal cross-sectional area is described below using a round hose cross-section.

Two methods are known for determining the internal cross-sectional area. Both methods have such a high measurement accuracy that the distribution of the measured values can be used to draw conclusions about the manufacturing tolerance.

The first method involves measuring the internal diameter of a hose using computer tomography. The measuring accuracy of the computer tomography is about 30 μm. To determine the tolerance of the internal cross-sectional area, the internal diameters must be measured. The internal cross-sectional areas can then be inferred from these measurements. The expected distribution is a Gaussian or normal distribution. This assumes that the distribution of the measured internal diameters around the nominal value extends symmetrically in both directions. The limit values, which cover the range in which 95% of the measured inside diameters lie, define the tolerance values of the inside diameter. The measurement is made at a minimum of two points on the hose. Preferably, these points are not close to one other. The most suitable procedure is to choose a first measuring point close to one end of the hose and to choose the second measuring point close to the other end of the hose.

A second method for determining the inner diameter is the measurement by allowing a fluid to flow through the hoses with identical, known boundary conditions. The volume flow can be inferred from the boundary conditions. This allows the resulting volume flow to be compared with the setpoint volume flow. The difference between these volume flows is due to the difference in internal cross-sectional area. The flow rate through a hose is proportional to its internal cross-sectional area. This measuring method requires that either a hose with known dimensional accuracy is used as a reference variable, or a volume flow to be achieved is used as a reference variable. The reference hose defines the target volume flow. The deviation of the measured volume flow rates of the remaining hoses from the target volume flow rate is due to the different internal cross-sectional area of the remaining hoses compared to the reference hose. Since, as mentioned above, the volume flow is proportional to the internal cross-sectional area, the difference in volume flow can be directly inferred from the difference in internal cross-sectional area. If only one reference variable is known, each measured volume flow must be compared with the reference variable. The deviation from the reference value determines the deviation of the internal cross-sectional area from the nominal internal cross-sectional area. The discrepancy in the volume flow is proportional to that in the internal cross-sectional area.

The volume flow here need not be described as a volume as a function of a unit of time, but can also use units of measurement other than those of time. These units of measurement can also be time-independent, such as the rotor revolution of a peristaltic pump. Thus, the volume flow can be specified as volume per rotor revolution of the peristaltic pump both as a comparative quantity and as a measured quantity. To determine whether a hose is within the tolerance range or not, a greater quantity of hoses of the same design must be measured. If at least 95% of all hoses measured show a value within the tolerance range, the hose is considered to be within the tolerance range. It is not possible to make a statement on the basis of a single measurement of a hose as to whether this hose is generally within a tolerance range or not.

Figure 7:
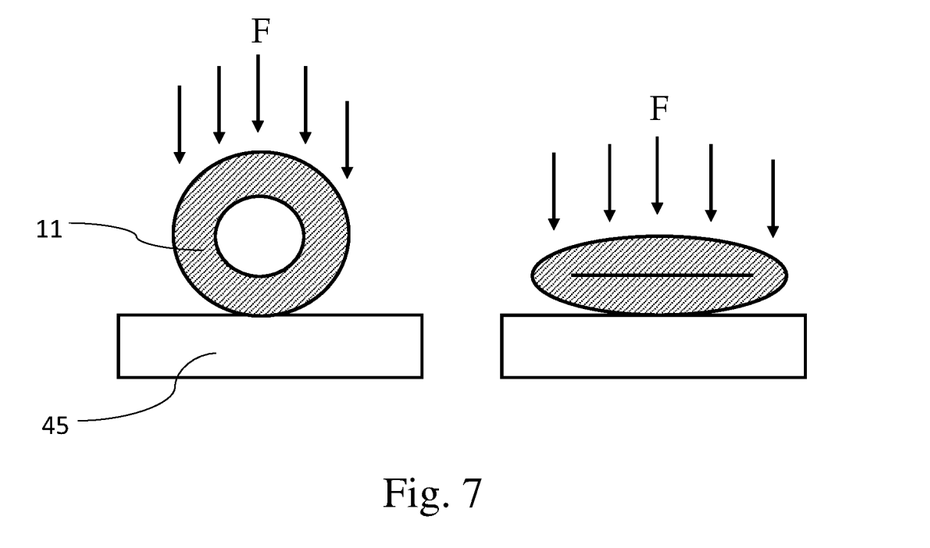
FIG. 7: cross-section of a hose in the open and closed states.

FIG. 7 shows a sequence of two illustrations showing the closing of a hose 11. The hose is arranged on a bar 45 of a rotor. The force F acting on the hose 11 is a result of the pretensioning force with which the hose 11 is stretched in the dispensing cartridge and the counterforce of the bar 45, which varies as the rotor moves. While the pretensioning force remains constant, the counterforce of the bar varies depending on its position. A cyclic opening and closing movement of the hose 11 therefore occurs as a result of the rotation of the rotor.

The amplitude of the opposing force exerted by the bar 45 cannot be changed. On the other hand, the pretensioning force with which the hose 11 is stretched on the dispensing cartridge can be set as desired. The pretensioning force can be used to influence the service life of the hose 11. The greater the pretensioning force, the shorter the service life of the hose 11.

The selection of the pretensioning force further depends on the geometry of the hose 11, in particular on its cross-sectional area. The larger the cross-sectional area of the hose 11, the greater the pretensioning force must be to ensure that the hose closes completely.

Another effect to be taken into account when dimensioning the hose 11 is the inertia and pressure of the fluid contained in the hose 11. When the force F exerted on the hose 11 by the pretensioning falls below a certain value, the hose 11 no longer closes completely because the internal pressure in the hose 11 exerts a greater force.

The hose 11 must have at least a certain diameter in order to ensure complete closure. If the pressure falls below this value, the force of the liquid in the hose alone will cause the hose to remain partially open at all times.

Taking into account these behaviors and rules, a range for the cross-sectional area is obtained within which the closure of the hose is guaranteed and the maximum service life of the hose 11 is ensured.

Tests and measurements have shown that at a pretensioning force of 1 to 10 N, the optimum service life for a hose with an inside diameter of about 0.9 mm is achieved by a wall thickness of about 0.5 mm. The greater the wall thickness, the greater the pretensioning force must be. Since the maximum service life is achieved with the smallest pretensioning force, the smallest possible wall thickness should be selected for the maximum service life. In order to achieve a maximum service life with a hose inner diameter of 0.15 mm to 1.5 mm, therefore, an ideal wall thickness of 0.3 to 2.2 mm, in particular of 0.3 to 1.2 mm, further preferably of 0.3 to 0.7 mm, is obtained.

A smaller inner diameter also requires a smaller wall thickness. Therefore, for a hose which closes when stretched over a rotor with a tensile force of 1 to 10 N, the ratio between its inside and outside diameter is specified. Ideally, the ratio between the inner and outer diameters of the hose is 0.3 to 0.6, preferably 0.4 to 0.55.

Using a Hose in Accordance with the Invention

A hose in accordance with the invention is provided to be attached to a dispensing cartridge via its thickenings. Preferably, several hoses are arranged in parallel within the dispensing cartridge. The production of the hoses by means of the injection molding process leads to very small tolerances for the inner diameter. Due to the small tolerance, the individual hoses do not need to be adjusted individually. At the same time, this also makes it possible to replace a single hose by another without having to make any changes to the dispensing cartridge. The hose in accordance with the invention is dimensioned and attached to the dispensing cartridge in such a way that the hose can close completely when operating in a peristaltic pump with only one rotor and without a hose bed. The hose is stretched over the rotor during operation in the peristaltic pump. The rotation of the rotor is responsible for the peristalsis. In this case, a hose in accordance with the invention is completely closed without having to rely on a counterforce in the form of a hose bed. The complete closure of the hose is made possible solely by the force compressing the hose. This is determined by the tension force of the hose over the rotor, the rotor geometry, and the dimensions of the hose. The hose must have a wall thickness sufficient for the mass of the wall to provide sufficient force to clamp the hose, thereby ensuring complete closure. As already described above, too great a tension force or too thin a wall thickness of the hose will lead to a reduction in the service life of the hose.

While the invention has been described above with reference to specific embodiments, it is apparent that changes, modifications, variations, and combinations may be made without departing from the spirit of the invention.

LIST OF REFERENCE NUMBERS

11 Hose
13, 13' Thickening on the hose
15, 15' End of the hose
17 Distance from the thickening to the end of the hose
19 Square side of a parallelepipedal thickening
21 Rectangular side of a parallelepipedal thickening
23 Longitudinal edges of the thickening
25 Recess at the thickening
27 Semicircular edge of the thickening
29 Tension elements 31 Adjusting screw
33 Dispensing cartridge
35, 35', 35", 35''' Cartridge
37 Hose connection
39 Second hose
41 Connector
43 Nozzle
45 Bar of the rotor

The invention claimed is:

1. A dispensing cassette for a peristaltic pump without a hose bed, said cassette comprising:
a first cartridge and second cartridge that are each configured to be mounted onto a peristaltic pump without a hose bed;
a plurality of one-piece, injection molded hoses (11) each mounted to the first cartridge and to second cartridge in parallel for placement in the peristaltic pump and for stretching over a rotor of the peristaltic pump and conveying a medium by external mechanical deformation of the respective hose by the rotor without pressing the hose against a wall,
each said hose (11) having a length of less than or equal to 200 mm between its ends; and
each of the hoses having a first thickening (13) and a second thickening (13'), wherein the first thickening and the second thickening of each hose are formed integrally with an outer surface of the respective hose and are located proximate to a respective end of the hose (11), wherein each hose including its first thickening and its second thickening are integrally formed of the same material, whereby when each hose is in a pretensioned state the first thickening and the second thickening are spaced apart at a fixed distance and the fixed distance between the thickenings is between 40 mm and 100 mm, and the ends of the hose extend beyond the respective thickenings;
wherein said first thickening for each hose is attached to the first cartridge and said second thickening for each hose is attached to the second cartridge, such that the plurality of hoses are attached in parallel between the first cartridge and the second cartridge and are over the rotor of the peristaltic pump to a desired tension when the first cartridge and the second cartridge are mounted onto the peristaltic pump;
the plurality of hoses (11) is manufactured by an injection molding process with a wall thickness from 0.3 mm to 1.2 mm and a circular internal cross-sectional area of from 0.07 to 2.6 mm$^2$ wherein the inner cross-sectional area has a tolerance of at most ±12.5%;
the plurality of hoses (11) further having a Shore hardness of from 35 to 65 Shore-A, the combination of these features allows the multiple hoses to be completely closed by the rotating rotor of the peristaltic pump when they are stretched over the rotor with a tensioning force of between 1 and 10 N without pressing them onto an opposing hose bed, and the individual hoses have substantially the same flow rates without the individual lengths of the hoses being adjusted with separate tensioning means.

2. The dispensing cassette in accordance with claim 1, characterized in that the material of the injection molded hoses has a Shore hardness of from 45 to 55 Shore-A.

3. The dispensing cassette in accordance with claim 1, characterized in that the material of the injection molded hoses comprises a plastic selected from the group consisting of polyvinyl chlorides (PVC).

4. The dispensing cassette in accordance with claim 1, characterized in that the material of the injection molded hoses comprises silicone.

5. The dispensing cassette in accordance with claim 1, characterized in that the injection molded hoses (11) have a length of 20 mm to 70 mm.

6. A dispensing cassette as recited in claim 1 further comprising connections between each respective injection molded hose and one of a plurality of feed hoses.

7. A dispensing cassette in accordance with claim 6, characterized in that the connections are by overmolding.

8. A dispensing cassette in accordance with claim 6, characterized in the connections are implemented using a plurality of connecting pieces (41) connecting each injection molded hose to a respective feed hose.

9. The dispensing cassette in accordance with claim 1 wherein when dispensing cassette is mounted in the pump and the injection molded hoses are pretensioned over the rotors, each hose in an open state and has an inside circular wall that is substantially concentric with an outside circular wall.

* * * * *

UNITED STATES PATENT AND TRADEMARK OFFICE
CERTIFICATE OF CORRECTION

PATENT NO. : 12,152,577 B2  
APPLICATION NO. : 17/467796  
DATED : November 26, 2024  
INVENTOR(S) : Daniel Shearer et al.

Page 1 of 1

It is certified that error appears in the above-identified patent and that said Letters Patent is hereby corrected as shown below:

In the Claims

Claim 1, Column 11, Line 16, before "second" insert -- the --;

Claim 9, Column 12, Line 39, after "when" insert -- the --;

Claim 9, Column 12, Line 41, after "hose" insert -- is --.

Signed and Sealed this  
Seventh Day of January, 2025

Derrick Brent  
*Acting Director of the United States Patent and Trademark Office*